US009711251B2

(12) United States Patent
Lee et al.

(10) Patent No.: US 9,711,251 B2
(45) Date of Patent: Jul. 18, 2017

(54) APPARATUS AND METHOD FOR VARIABLE ANGLE SLANT HOLE COLLIMATOR

(71) Applicant: JEFFERSON SCIENCE ASSOCIATES, LLC, Newport News, VA (US)

(72) Inventors: Seung Joon Lee, Poquoson, VA (US); Brian J. Kross, Yorktown, VA (US); John E. McKisson, Williamsburg, VA (US)

(73) Assignee: JEFFERSON SCIENCE ASSOCIATES, LLC, Newport News, VA (US)

( * ) Notice: Subject to any disclaimer, the term of this patent is extended or adjusted under 35 U.S.C. 154(b) by 240 days.

(21) Appl. No.: 14/818,839

(22) Filed: Aug. 5, 2015

(65) Prior Publication Data
US 2017/0040077 A1    Feb. 9, 2017

(51) Int. Cl.
*G21K 1/04* (2006.01)
*G21K 1/02* (2006.01)

(52) U.S. Cl.
CPC ............... *G21K 1/04* (2013.01); *G21K 1/025* (2013.01)

(58) Field of Classification Search
CPC .............................. G21K 1/046; G21K 1/025
USPC ................................. 378/145–153; 250/505.1
See application file for complete search history.

(56) References Cited

U.S. PATENT DOCUMENTS

| 4,419,585 | A * | 12/1983 | Strauss ................. G02B 5/005 250/363.1 |
| 5,436,958 | A * | 7/1995 | Taylor ..................... G21K 1/04 250/363.1 |
| 6,424,693 | B1 | 7/2002 | Weisenberger |
| 7,596,209 | B2 | 9/2009 | Perkins |
| 2012/0326059 | A1 | 12/2012 | Hawman et al. |
| 2013/0158389 | A1 | 6/2013 | O'Connor |

OTHER PUBLICATIONS

Gaopan, Olga, Molecular Imaging of the Breast Using a Variable-Angle Slant-Hole Collimator, Jun. 4, 2014, pp. 1143-1152, vol. 61, No. 3, IEE Transactions on Nuclear Science.

* cited by examiner

*Primary Examiner* — Courtney Thomas

(57) ABSTRACT

A variable angle slant hole (VASH) collimator for providing collimation of high energy photons such as gamma rays during radiological imaging of humans. The VASH collimator includes a stack of multiple collimator leaves and a means of quickly aligning each leaf to provide various projection angles. Rather than rotate the detector around the subject, the VASH collimator enables the detector to remain stationary while the projection angle of the collimator is varied for tomographic acquisition. High collimator efficiency is achieved by maintaining the leaves in accurate alignment through the various projection angles. Individual leaves include unique angled cuts to maintain a precise target collimation angle. Matching wedge blocks driven by two actuators with twin-lead screws accurately position each leaf in the stack resulting in the precise target collimation angle. A computer interface with the actuators enables precise control of the projection angle of the collimator.

20 Claims, 6 Drawing Sheets

APPARATUS AND METHOD FOR VARIABLE ANGLE SLANT HOLE COLLIMATOR

GOVERNMENT LICENSE RIGHTS

This invention was made with government support under Management and Operating Contract No. DE-AC05-06OR23177 awarded by the Department of Energy. The United States Government has certain rights in the invention.

FIELD OF THE INVENTION

The present invention relates to radiation collimators and gamma and x-ray photon systems as applied to medical radiology and nuclear medicine.

BACKGROUND OF THE INVENTION

In radiation imaging, collimators are used to limit the passage of radiation beams to a specific angle in order to minimize detection of beams of scattered or secondary radiation. Single angle collimation provides 2-dimensional (2D) projection of radiation sources on an imager while the combining of multi angle projections provides 3-dimensional (3D) position of radiation sources by image reconstruction techniques. Hence, it is more desirable to achieve 3D images particularly in clinical nuclear imaging. Devices have been proposed for multi angle projection imagers using multiple detectors at different positions, or by moving the position of a single detector, or by fixing the location of a detector and using multiple collimators each of which has a different collimation angle. It is not always feasible to combine aspects of these methods due to physical interference with the imaging target. Previously proposed multi angle collimators typically include either variable angle slant hole (VASH) collimators or multi-view collimators.

Although the VASH provides an adjustable angle of collimation, the reported alignment mechanism of the multiple leaves clearly does not provide accurate alignment of each leaf, thereby resulting in a reduced size of the openings and an inaccurate collimation angle that reduces the output image quality.

Accordingly, it would be desirable to provide a multiple leaf collimator in which the openings are accurately aligned, that maintains a constant collimation angle, and thus achieves high output image quality.

OBJECT OF THE INVENTION

It is therefore an object of the present invention to provide a variable angle slant hole (VASH) collimator that enables accurate tomographic acquisition by multiple angle projection while the detector remains stationary.

A second object is to provide a multiple leaf collimator that provides multiple views through the breast, thyroid, heart, or similar body part.

A further object of the invention is to provide an improved VASH actuation device that eliminates mechanisms adjacent the patient. The compact nature of the multi-leaf collimator and the fact that the mechanism can be positioned under covers on the side of the detector, away from the patient, makes it inherently safer to operate. This contributes greatly to the physical and emotional comfort of the patient. This is a significant improvement over prior mechanisms that use knife edge actuators, such as in breast imaging, in which the breast must be positioned between two knife blades.

A further object of the invention is to provide a multi-leaf collimator in which the openings can be maintained at a constant collimation angle and thus achieves high output image quality.

A further object of the invention is to provide a multi-leaf collimator that eliminates the need to rotate the detector.

A further object of the invention is to provide a multi-leaf collimator that can be adjusted to various viewing angles very quickly and with a high degree of precision.

A further object of the invention is to provide a multi-leaf collimator in which the aperture alignment is maintained and the motor doesn't strain when the collimator stack is turned vertically.

A further object of the invention is to provide a collimator in which the viewing angle can be changed very quickly to limit the radiation dose to the patient while acquiring the data for tomographic imaging.

A further object of the invention is to minimize the amount of time for acquiring multiple angle views of a patient that has been administered a radioisotope.

A further object of the invention is to provide a variable angle slant hole collimator that is compact in size to enable easy handling and turning to different orientations with respect to the patient.

BRIEF SUMMARY OF THE INVENTION

A variable angle slant hole (VASH) collimator provides collimation of high energy photon such as gamma ray used for radiological imaging of human. The VASH collimator is consist of multiple collimator leaves and alignment of each leave can provide various projection angles. Rather than rotate the detector around the subject, the VASH collimator allows tomographic acquisition while the detector remains stationary by multiple angle projection. An accurate alignment of leaves is required to provide maximum collimation efficiency. Individual leaf has own angled cut on each side and face matching wedge blocks driven by two actuators with twin-lead screws is providing an accurate position of each leaf resulting target collimation angle. Continuous collimation angle can be achieved by position control of wedge block.

DETAILED DESCRIPTION

Figure 1:
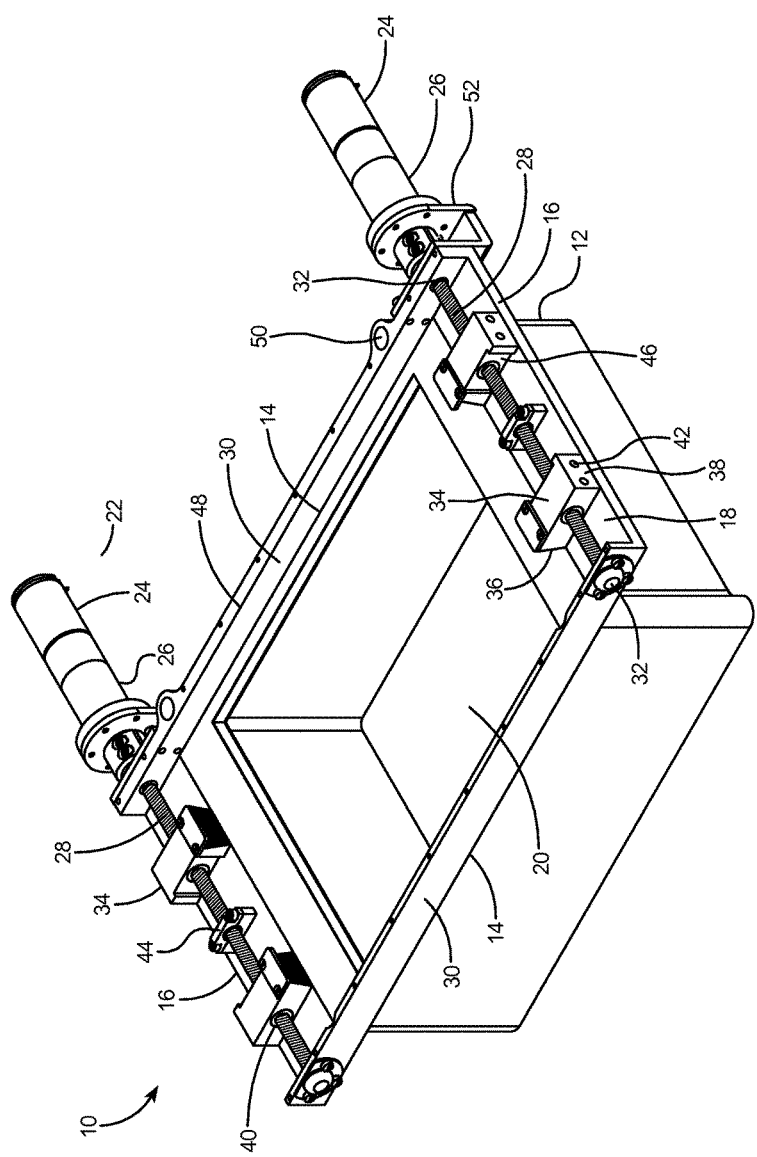
FIG. 1 is a top isometric view of the frame and driving mechanism for a variable angle slant hole (VASH) collimator according to the present invention.

With reference to FIG. 1, the present invention is a compact and efficient multi-leaf variable angle slant hole (VASH) collimator 10 in which the viewing angle of the apertures can be rapidly and accurately changed to provide various projection angles for 2-dimensional (2D) and 3-dimensional (3D) image reconstruction techniques. The VASH collimator 10 includes a frame 12 with opposing sides 14, opposing ends 16, and a front panel 18 with an opening 20 therein. A means 22 for positioning a plurality of collimator leaves (not shown) includes two motors 24 coupled by a gearbox 26 to a lead screw 28 at each end of the frame 12.

Two stack alignment rails 30, which will serve as guides for a stack of collimator leaves, extend along each side 14 of the frame. Two end bearings 32 positioned in each end of the rails 30 form paired end bearings that are axially aligned and enable rotation of the lead screws 28 with respect to the rails and frame. Two wedge blocks 34 are positioned on each lead screw 28 at the two ends 16 of the frame 12. The wedge blocks 34 include an inner end 36 and an outer end 38. A drive nut 40 is embedded in each wedge block to accommodate the screw threads of the lead screws 28. The outer end 38 of each wedge block 34 includes set screws 42 for locking each wedge block to its respective drive nut 40. A pillow block 44 supports each lead screw approximately mid-way between the two end bearings 32. Each wedge block 34 includes a clearance notch 46 for accommodating the pillow blocks 44 at full inward travel of the wedge blocks. A side mount 48 extends from one side 14 of the frame 12 and includes two bores 50 therein to accommodate attachments for imaging specific body parts, such as compression paddles (not shown) for breast imaging. One of the rails 30 includes two brackets 52 for mounting of the gearboxes 26 and motors 24 thereto.

Figure 2:
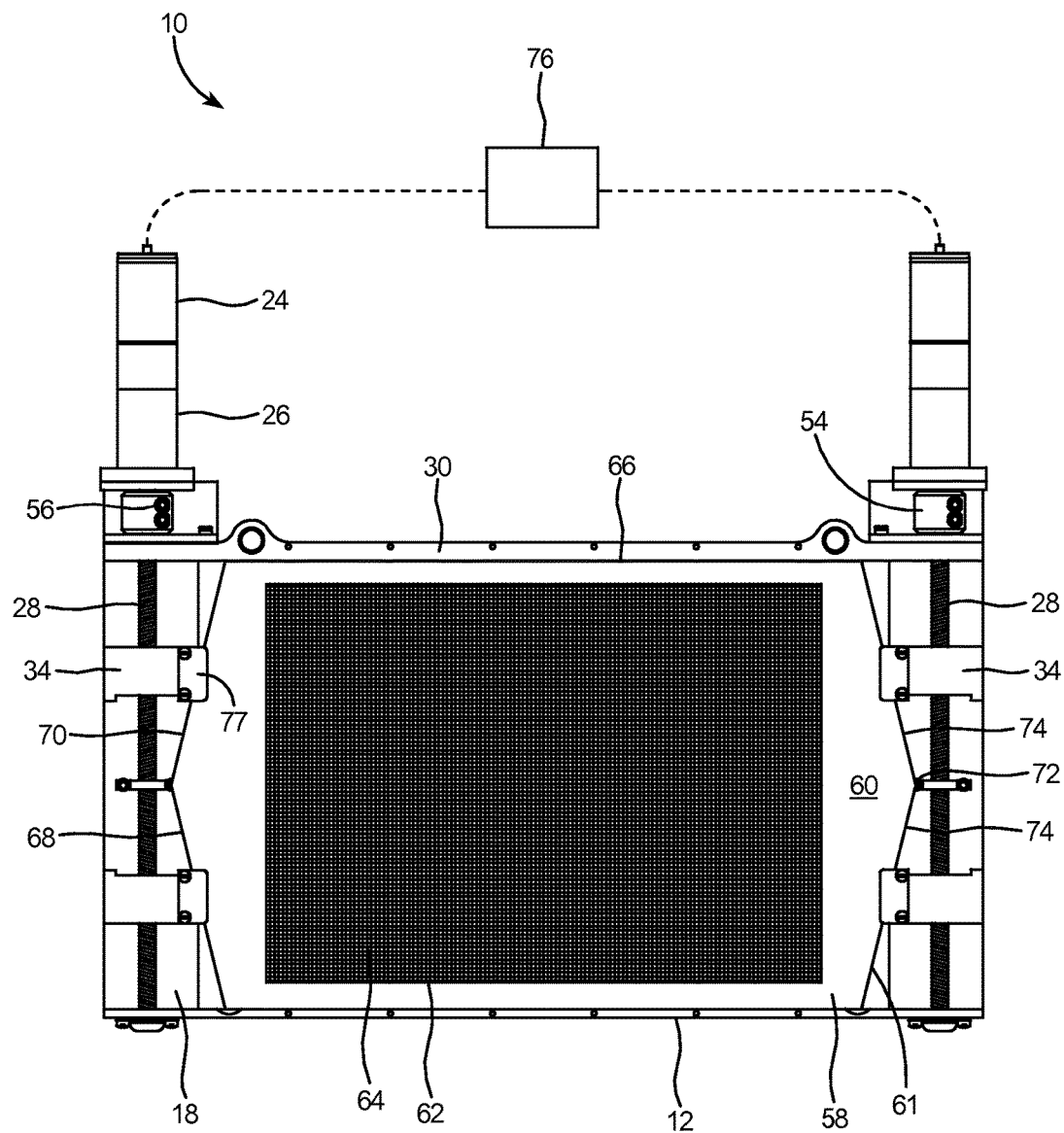
FIG. 2 is a top view of the VASH collimator including the collimator stack, the frame, and the driving mechanism.

Referring to FIG. 2, a coupler 54 including one or more screws 56 secures each motor 24 and gearbox 26 to their respective lead screw 28. A plurality of substantially planar leaves, of which the top leaf 58 having a face 60 is visible, are stacked against the front panel 18 to form a stack 61 of leaves. An array 62 of apertures 64 are arranged in an identical pattern in each of the leaves 58, with the leaves capable of alignment in an initial position wherein the apertures 64 in the leaves are axially aligned with one another and at 90° with respect to the face 60 of the top leaf. Each leaf 58 includes sides 66 and ends 68. The rails 30 maintain the contact with the sides 66 of the leaves 58 thus keeping the stack of leaves in alignment. The ends 68 of each leaf 58 include an angled cut 70 that is unique to that leaf. Most preferably the angled cut 70 on the ends of the leaves includes a substantially central apex 72 and two angled surfaces 74 extending to the sides 66 of each leaf. The bottom leaf (not shown) is preferably not angled, but includes ends that are at 90° with respect to its sides. A computer interface 76 may be used for controlling and synchronizing the direction of rotation of each of the motors 24 to change the position of the leaves 58 and thus the alignment of the apertures 64 to a desired slant angle. A stack cover plate 77 extends from each wedge block 34 and maintains the stack 61 of leaves 58 in place on the frame 12.

Figure 3:
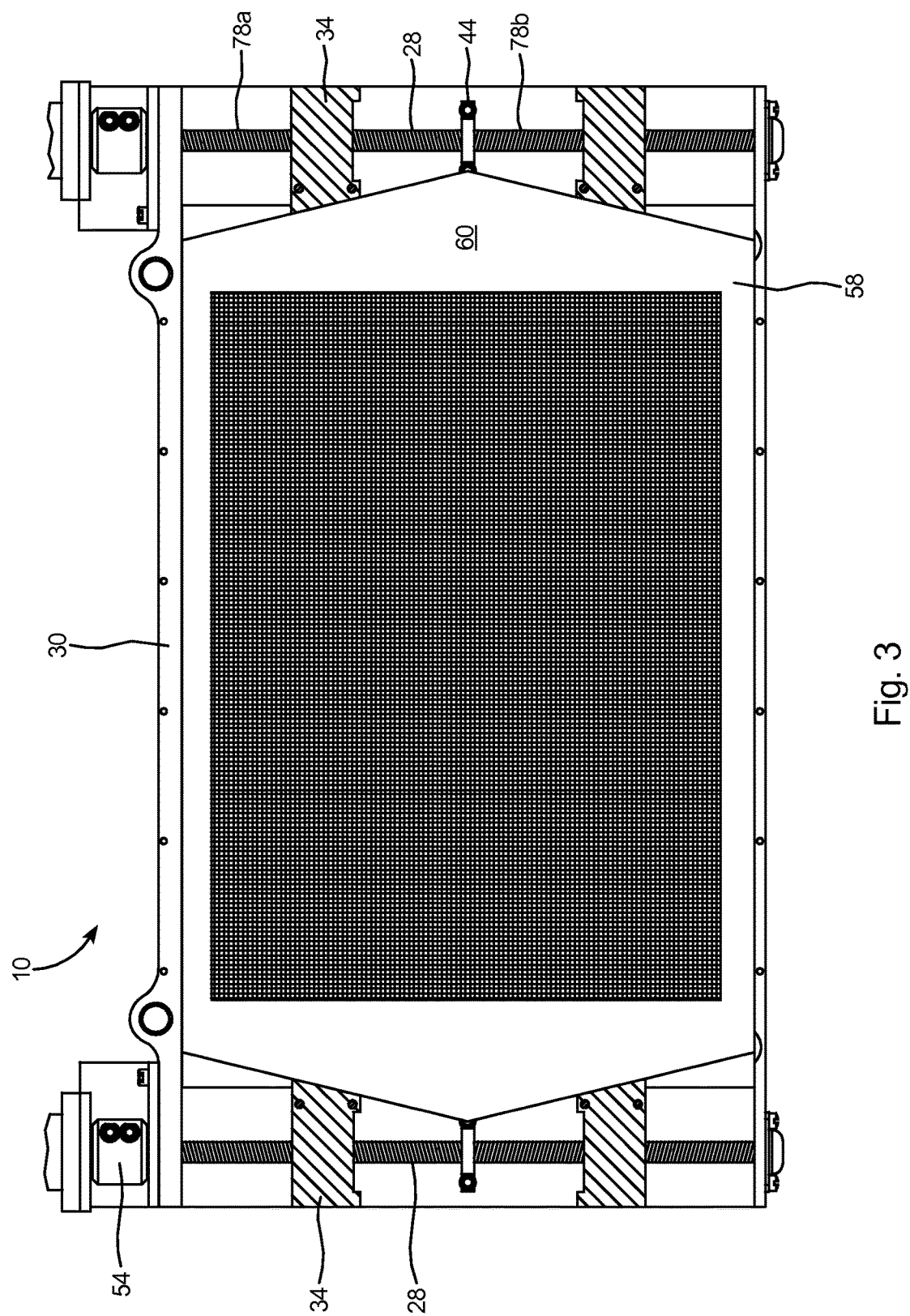
FIG. 3 is a top view of the VASH collimator with the motor and gearbox portion of the drive mechanism and the stack cover plates cut away.

Preferably, with reference to FIG. 3, a reverse thread is included on the shaft of the lead screws 28 on opposing sides of the pillow block 44, such as the screw threads on one half of the lead screws are right-hand threaded 78a and the screw threads on the opposing half of the lead screws are left-hand threaded 78b.

Figure 4:
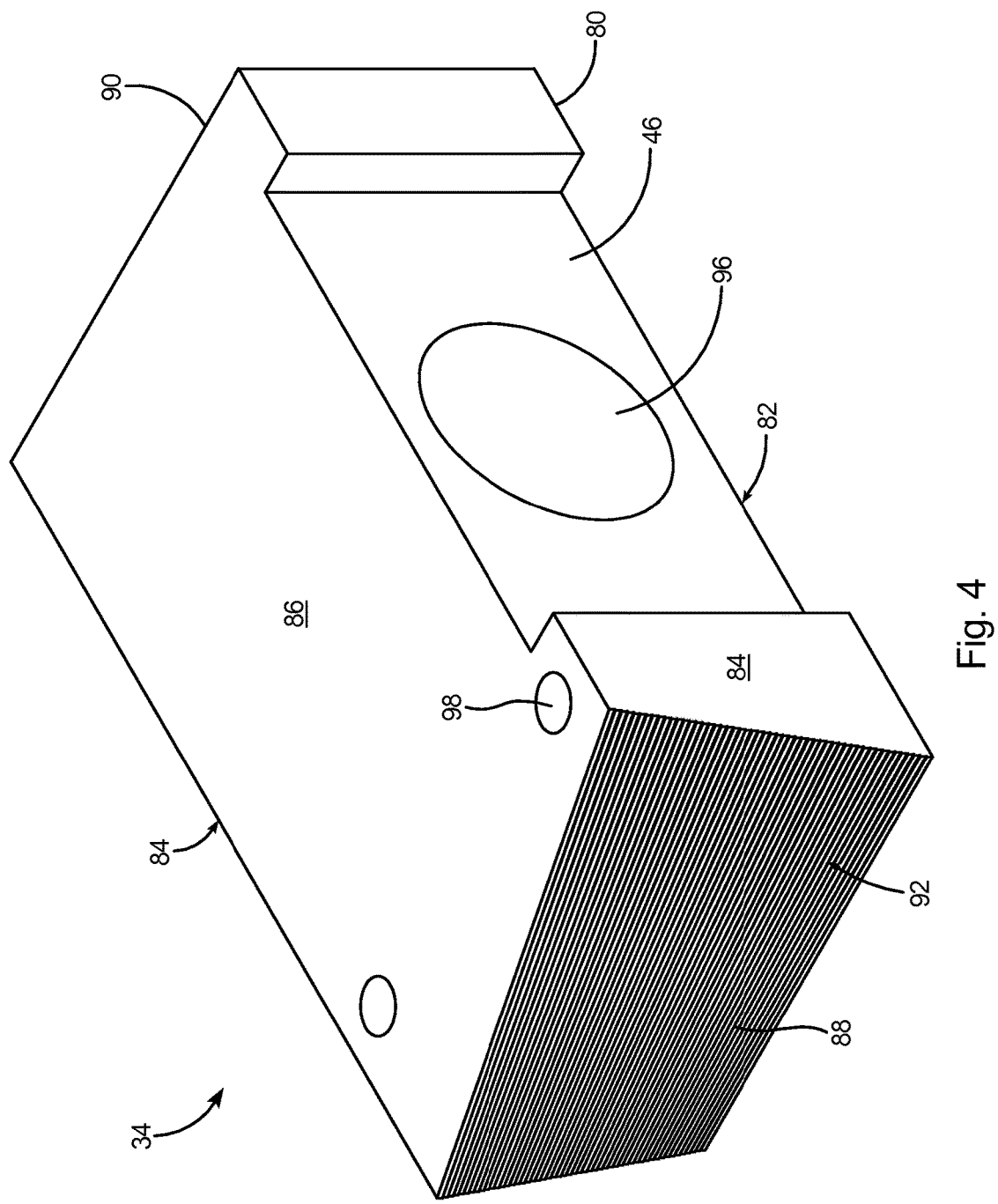
FIG. 4 is an isometric view of a wedge block according to the present invention.
Figure 5:
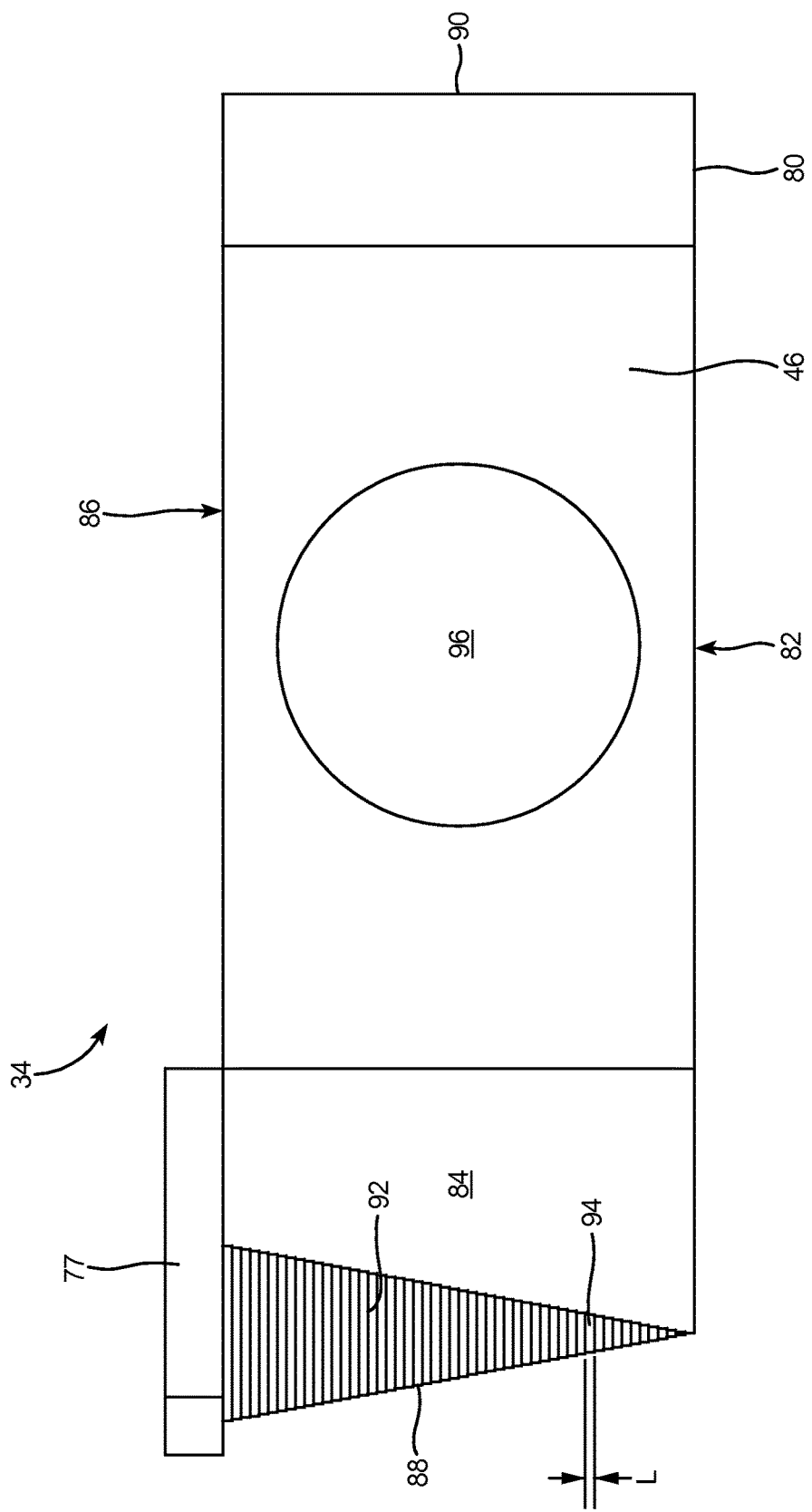
FIG. 5 is a side view of a wedge block according to the present invention.

Referring to FIGS. 4 and 5, each wedge block 34 includes a wedge body 80 having a flat bottom surface 82, two sides 84, a top 86, and a first end 88 second end 90. The bottom surface 92 is at 90 degrees with respect to the sides 84 and the first end 88 is cut with a desired angle. A stepped edge 92 is provided on the first end 88 of the wedge block. Preferably, the length L of each step 94 in the stepped edge matches the thickness of a corresponding leaf in the stack of leaves held by the frame 12. The wedge block 34 further includes a side bore 96 for accommodating the drive nut 40 and two apertures 98 for screw attachment of the cover plate 77 (see FIG. 2).

Figure 8:
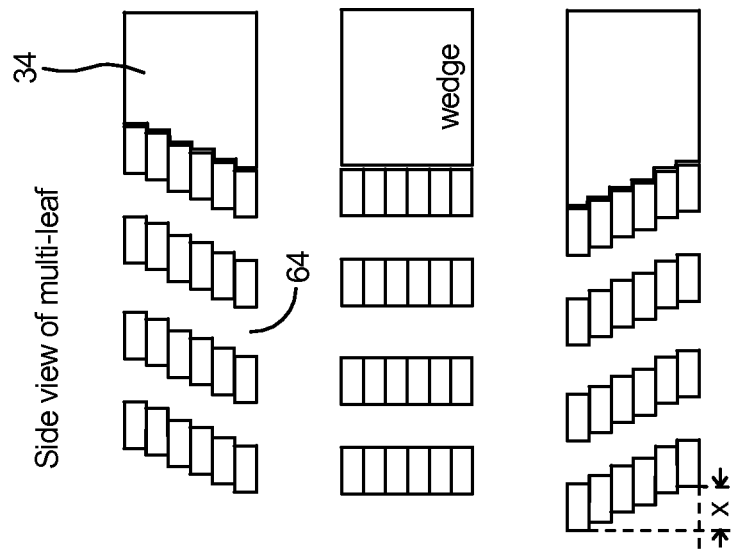
FIG. 8 is a side view depicting multi-leaf motion of a VASH collimator according to the present invention.
Figure 7:
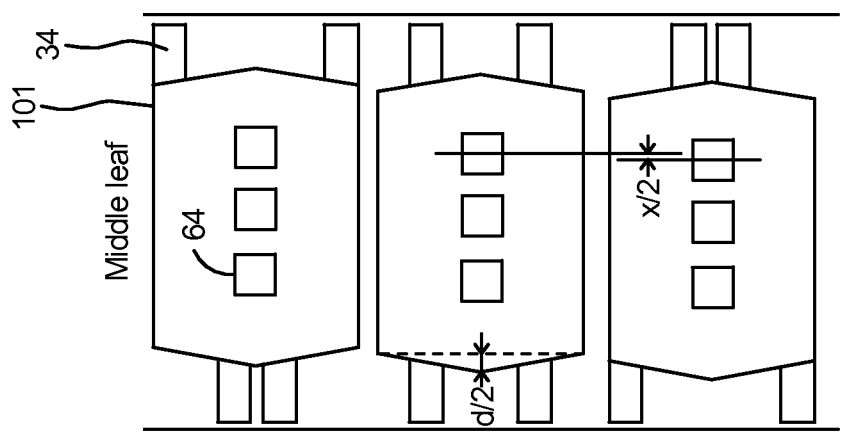
FIG. 7 is a top view depicting the movement of the middle leaf of a VASH collimator according to the present invention.
Figure 6:
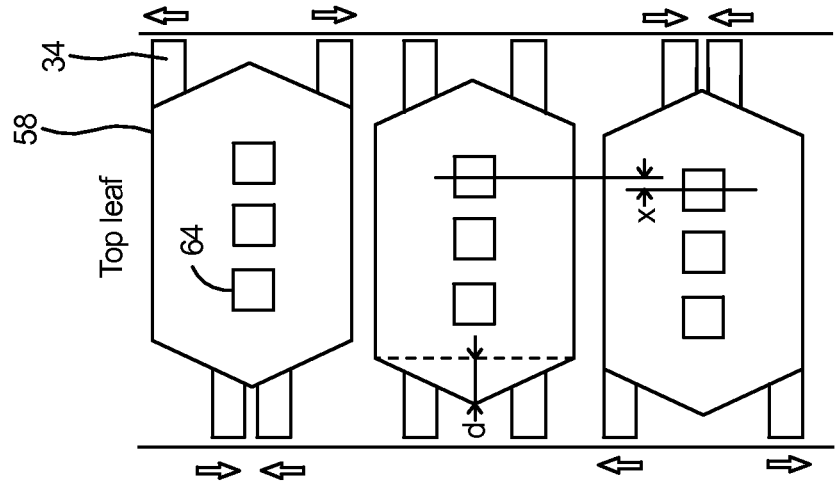
FIG. 6 is a top view depicting the movement of the top leaf of a VASH collimator according to the present invention.

FIGS. 6-8 depict the actuation mechanism of the VASH collimator 10 including movement of the top leaf (FIG. 6), movement of the middle leaf (FIG. 7), and a side view of multi-leaf motion (FIG. 8). The top leaf 58 and middle leaf 101 have different side profiles, with the top leaf 58 including a length d and the middle leaf 101 including a length d/2, resulting in a displacement of x and x/2 for the two leaves, respectively. A continuous slant angle can be achieved by positioning of the four wedge blocks 34. The bottom leaf with a straight side does not move. The other leaves have an angled cut and the tangent value of each angle is a linear step to make the stepped displacement linear. The sliding wedge blocks 34 each include a stepped profile with each step being the same thickness as a corresponding leaf so that there is no gap between the sliding wedge 34 and the side of each leaf as shown in FIG. 8. This will provide a maximum efficiency for wedging motion. The desired angle of the slant hole collimation is selected by moving the four sliding wedges 34, such that the motion moves each leaf in one direction with a different displacement.

As shown in FIG. 1, the two wedge blocks 34 on each end 16 are moving in opposite directions of each other by the rotation of the twin-lead screw 28. At the same time, the two wedge blocks 34 on the opposing end 16 are moving in the opposite direction of those on the first end in order to compensate leaf motion. There is a pillow block 44 at the middle of each twin-lead screw to prevent bending of the lead screws 28. Each wedge block 34 has a cover plate 77 to ensure all leaves are stacked at the same height as the wedge blocks 34. Accurate motion and counter motion of the wedge blocks 34 at each end 16 of the VASH collimator provides an exact amount of space for each leaf resulting in an accurate positioning and setting of the collimation angle for all the apertures in the leaves.

The range of slant angles is determined by the cut profile of opposing sides of each leaf, the matching profile for the sliding wedge block 34, and by the sliding/travel range of the wedge blocks. Since the displacement by wedge motion of each leaf is continuous, the collimation angle can be set continuously within a pre-defined range. On one end 16 of the leaves, the two wedges 34 are moving in opposite direction of those on the opposing end of the leaves to balance the force. Actuators for the twin-lead screws 28 are driven by a motor 24 with a high ratio gear box 26.

The present invention further includes a method for aligning a collimator, the method including:
 a. providing a frame including side rails, and two ends;
 b. providing twin lead screws, two wedge blocks on each lead screw, coupling nuts, and a plurality of leaves with an array of apertures therein;
 c. moving the wedge blocks and coupling nuts to the side rails of the frame;

d. fixing the wedge blocks to the coupling nuts;

e. stacking the leaves in the frame to form a multi-leaf stack;

f. adjusting the position of two wedge blocks on a first end of the frame toward each other until they are in contact with each other; and g. moving the four wedge blocks in the desired direction with the desired distance, at the same speed, for setting the slant angle of the multi-leaf stack.

Preferably the leaves 58 and the frame 12 are constructed of tungsten primarily for its ability to stop radiation penetration, and also for non-dulling properties, abrasion resistance, and mechanical strength. Preferably the apertures 64 are photo-etched square holes, but may be hexagonal or circular shaped. The size of the apertures can be selected for the desired levels of sensitivity and resolution, with larger apertures leading to higher sensitivity but lowering the resolution. The thickness of the leaves may also be selected for the application, with thicker leaves leading to lower resolution. The energy of the radioactive tracer determines the number of leaves required, with a taller stack leading to higher resolution and a shorter stack leading to higher sensitivity. Although the disclosure herein depicts the apertures parallel to one another, it is within the scope of the invention to provide apertures at various angles, such as sloping the apertures higher toward the edge of each leaf.

The theoretical analysis of VASH is as follows:

(a) The maximum travel range of wedge motion is limited by following equation $$Tw = 0.5*Wc - Wb$$

where Tw is the travel range of wedge block, Wc is the width of collimator leaf, and Wb is the width of wedge block.

(b) The profile of the top leaf is defined by P which is the half of the difference between the longest length of leaf and the shortest length of leaf. (d in FIG. 6).

(c) Movement of each leaf from the zero degree (perpendicular to the detector) collimation to the maximum angle, M, is defined by following $$M = P*Tw/Wc$$

(d) The maximum collimation angle A is defined by $$A = \tan-1(M/((N-1)*T))$$

where N is the number of the leaf and T is the thickness of a single leaf.

Example

As an example, a VASH collimator constructed for breast imaging included 50 leaves that were each 0.25 mm in thickness for a total stack height of 12.5 mm. A tungsten frame held the leaves. Two lead screws, each being ½ right-hand threaded and ½ being left-hand threaded, were driven by a motor and gearbox to change the viewing angle +/−28 degrees. There are two end bearings per end, one supporting each end of each screw. A pillow block supported each screw in the center. A drive nut was embedded in each wedge block to accommodate the screw threads of the lead screws. Each wedge included a clearance notch for pillow block clearance. A gamma transparent cover was used to cover the collimator stack, both for keeping the apertures clear and shielding the patient from moving parts of the collimator. A brushless motor available from Micromo of Clearwater, Fla., was used to power the lead screws and wedge blocks. The gearing ratio of the motor and gearbox was 134:1. The motion of the wedges was limited at each end of the lead screws by high current. Driving the motors required 100 mA for the first motor and 150 mA the second motor. The end pushing the wedge blocks to the center was the drive motor. The drive switches end-to-end to change the direction of leaves and thus the viewing angle. In the preferred embodiment, an elapsed time of one minute was required to move the viewing angle from +28 to −28. If preferred, by changing the gearbox, the elapsed time can be reduced to 20 seconds. Four (2×2) apertures were provided to each scintillator element.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments herein were chosen and described in order to best explain the principles of the invention and the practical application, and to enable others of ordinary skill in the art to understand the invention for various embodiments with various modifications as are suited to the particular use contemplated.

What is claimed is:

1. A variable angle slant hole collimator, comprising:
   a frame including opposing sides, opposing ends, and a front panel having an opening therein;
   a plurality of substantially planar leaves stacked against said front panel in said frame, said stack including a top leaf with a face;
   an array of apertures arranged in an identical pattern in each of said leaves, said leaves capable of alignment in an initial position wherein said apertures in said leaves are axially aligned with one another and at 90° with respect to the face of the top leaf;
   a means for positioning each of said leaves in said stack of said leaves in a controlled manner such that each leaf slides at a predetermined rate with respect to the surrounding leaves in the stack; and
   said means for positioning said stack includes a lead screw and two wedge blocks on each end of said frame and an actuator for driving said lead screws.

2. The variable angle slant hole collimator of claim 1, further comprising
   two ends and two sides on each leaf in said stack of leaves; and
   said ends of each leaf include an angled cut that is unique to that leaf.

3. The variable angle slant hole collimator of claim 1, including
   a bottom leaf in contact with said front panel; and
   said bottom leaf includes ends and sides that are at a 90° angle to each other.

4. The variable angle slant hole collimator of claim 1, further comprising
   a rail extending along each side of said frame;
   an end bearing at opposing ends of said rails forming a pair of axially aligned end bearings at each end of said frame; and
   one of said lead screws extending through each of said pairs of end bearings.

5. The variable angle slant hole collimator of claim 1, wherein said actuator further comprises
   a motor;
   a gearbox; and
   a computer interface for controlling the direction of rotation of said motor.

6. The variable angle slant hole collimator of claim 1, further comprising
screw threads on said lead screws; and
a drive nut embedded in each of said wedges to accommodate the screw threads of the lead screws.

7. The variable angle slant hole collimator of claim 6, further comprising a pillow block secured to said front panel for supporting said lead screw between each of said wedges.

8. The variable angle slant hole collimator of claim 7, wherein the screw threads on one half of said lead screws are right-hand threaded and the screw threads on the opposing half of said lead screws are left-hand threaded.

9. The variable angle slant hole collimator of claim 1, wherein each of said wedges includes a wedge body having a flat bottom surface, two sides, a top, and first end and a second end.

10. The variable angle slant hole collimator of claim 9, further comprising a plate extending from said top of said wedge block.

11. The variable angle slant hole collimator of claim 10, further comprising a stepped edge on said first end of said wedge block.

12. The variable angle slant hole collimator of claim 11, wherein the length of each step in said stepped edge of said wedge matches the width of a corresponding leaf in said stack of leaves.

13. The variable angle slant hole collimator of claim 2, wherein said angled cut on said ends of said leaves includes a substantially central apex and two angled surfaces extending to said sides of said leaves.

14. A method for aligning a multi-leaf collimator, comprising the steps of:
providing a frame including side rails, and two ends;
providing twin lead screws, two wedge blocks on each lead screw, coupling nuts, and a plurality of leaves with an array of apertures therein;
moving said wedge blocks and coupling nuts to the side rails of said frame;
fixing the wedge blocks to the coupling nuts;
stacking said leaves in said frame to form a multi-leaf stack;
adjusting the position of two wedge blocks on a first end of said frame toward each other until they are in contact with each other; and
moving the four wedge blocks in the desired direction with the desired distance, at the same speed, for setting a slant angle of the multi-leaf stack.

15. The method of claim 14 further wherein fixing the wedge blocks to the coupling nuts includes
providing a plurality of set screws;
setting the initial positions of said wedge blocks by sliding the wedge blocks on the coupling nuts; and
securing two set-screws through each wedge block to lock said wedge block to said coupling nut.

16. The method of claim 14 wherein said moving of said wedge blocks includes matching the speed and distance traversed of each wedge block.

17. The method of claim 14 which includes synchronizing the counter motion of each of said wedge blocks to avoid a gap between the edge of each leaf and each wedge block.

18. The method of claim 14, further comprising
providing a stepped edge on a first end of said wedge block; and
matching the length of each step on said stepped edge of said wedge block equal to the width of a corresponding leaf in said stack of leaves.

19. The method of claim 14, further comprising
providing an end on each leaf in said stack of leaves; and
providing an angled cut on the end of each leaf.

20. The method of claim 19 wherein said angled cut on said ends of said leaves includes a substantially central apex and two angled surfaces extending to said sides of said leaves.

* * * * *